United States Patent [19]

Lounsbury, Sr. et al.

[11] Patent Number: Plant 7,644

[45] Date of Patent: Sep. 10, 1991

[54] GRAPVINE NAMED KAT.E.LIN

[76] Inventors: William L. Lounsbury, Sr., 1016 Cedar St., Dunnville, Ontario, Canada, N1A 2K5; Maurice W. Lounsbury, 187 Margaret St., Smithville, Ontario, Canada, L0R 2A0

[21] Appl. No.: 406,921

[22] Filed: Sep. 1, 1989

[51] Int. Cl.[5] ..... A01H 5/00

[52] U.S. Cl. ..... Plt./47

[58] Field of Search ..... Plt. 47

[56] References Cited

U.S. PATENT DOCUMENTS

| | | | |
|---|---|---|---|
| P.P. 42 | 11/1932 | Wiederkehr | Plt. 47 |
| P.P. 1,895 | 1/1960 | Thornburg | Plt. 47 |
| P.P. 4,787 | 11/1981 | Olmo et al. | Plt. 47 |
| P.P. 6,464 | 12/1988 | Karniel | Plt. 47 |

OTHER PUBLICATIONS

Hedrick, U. P., "617 Concord", *Systematic Pomology*, The MacMillan Co., N.Y., 1925, pp. 401 and 402.

*Primary Examiner*—James R. Feyrer

*Attorney, Agent, or Firm*—Browdy & Neimark

[57] ABSTRACT

A new and distinct asexually reproduced grapevine variety, as illustrated and described, is vigorous and highly productive, ripens early before frost, withstands temperatures below −18° C., fruits in fairly large open bunches with large shoulders, the fruit being red to dark maroon/oxblood red with a heavy bloom and having one of the highest Brix or sugar test of any labrusca grape reported in the Grape and Wine Research Summary for 1984 published by the Horticultural Research Institute of Ontario, Vineland Station, Ontario, Canada. The plant is resistant to mildew and does not require thinning. The fruit has a long shelf life and has proven to be excellent for jam, jelly and sweet, dessert wine.

6 Drawing Sheets

The present invention relates to a new and distinct variety of grapevine, named "Kat.E.Lin", which was discovered by us as a mutant of the Concord (Labrusca) variety, said discovery having occurred in our vineyard at Smithville, Ontario, Canada.

This new grape is characterized by early ripening fruit which matures well before frost in Ontario, Canada; by its ability to withstand temperatures below −18° C.; by its large open bunches of fruit which are easily sprayed and mechanically harvested; by its fruit colour which is dark maroon red with a heavy bloom; by its large shouldered bunches; by its very high sugar content; and by its excellent rating for sweet dessert wine, jelly and table use.

THE DRAWINGS

FIG. 1 is a drawing of a leaf showing the various parts measured and angles calculated for the numerical comparison of leaf shapes as outlined in the detailed description of the foliage (reference: Cépages et Vignobles de France, Tome I - Les Vignes Américaines; Imprimerie Charles Déhan, Paris, 1988).

FIG. 2*a* is a tracing of the petiolar sinus of type leaves of Kat.E.Lin.

FIG. 2*b* is a tracing of the petiolar sinus of type leaves of Concord.

FIG. 3*a* is a tracing of the dentations of type leaves of Kat.E.Lin.

FIG. 3*b* is a tracing of the dentations of type leaves of Concord.

DETAILED DESCRIPTION

The present mutant was discovered in our own vineyard at Smithville, Ontario, Canada in the 1960 growin season among twenty-five acres of Concord grapes which had been planted in the year 1925. It took three years for the original vine to bear fruit. Cuttings were taken in the fall of 1960, planted in 1961 and bore fruit in 1964. Propagation was carried out by taking two or three node cuttings in February, bundling in 10's and burying upsidedown in the ground, covered by two inches of soil. Cuttings were replanted in a nursery row eight weeks later.

Comparison With A Standard (Concord) Grown at the Same Relative Location

All colour references are from The Royal Horticultural Society Colour Charts (The Royal Horticultural Society, London. copyright 1966), henceforth called R.H.S.C.C.

Figure 1:
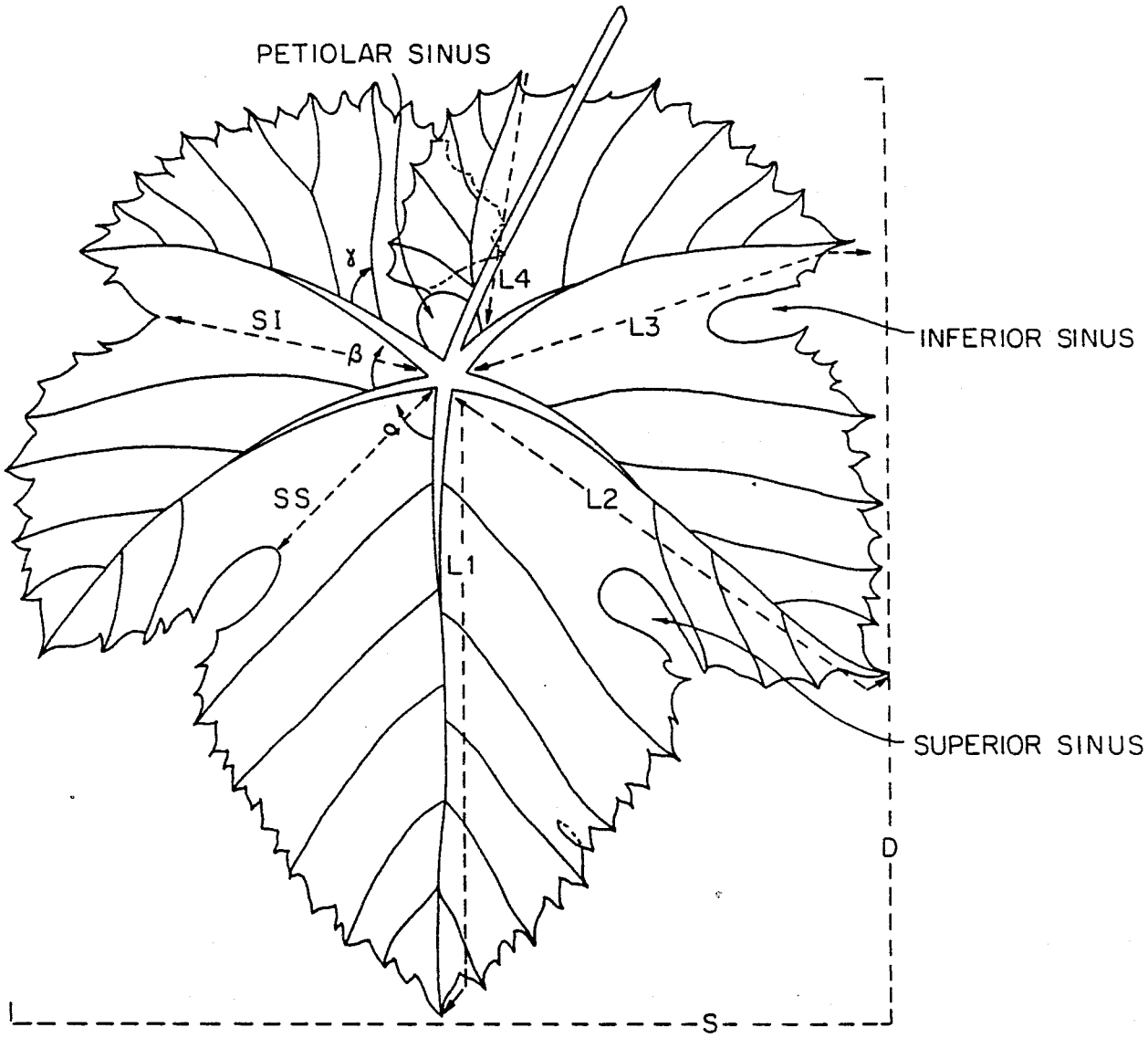

All foliage measurements and description are based on 10 leaves from the mid-section of a mature cane and foolow the ampelographic definitions of Galet (P. Galet, Cépages et Vignobles de France, Tome I - Les Vignes Américaines; Imprimerie Charles Déhan, Paris, 1988). See FIG. 1 for general terms of reference.

Figure 3A:
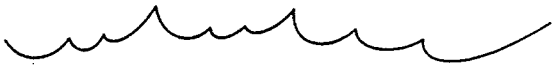
Figure 3A:
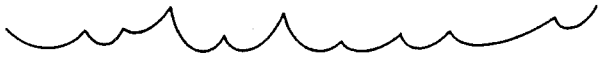
Figure 3A:
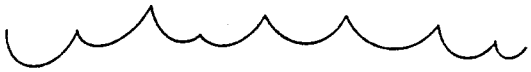
Figure 3A:
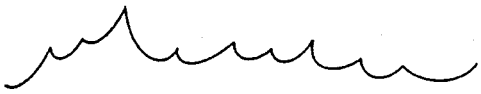
Figure 3A:
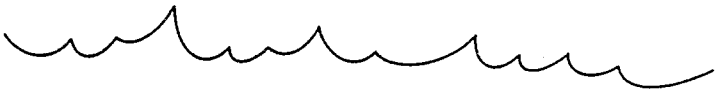
Figure 3A:
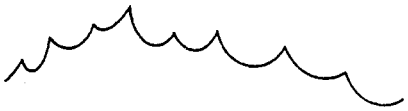
Figure 3A:
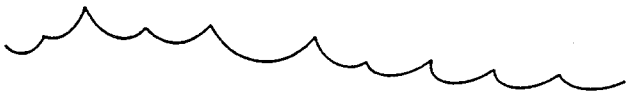
Figure 3B:
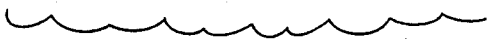
Figure 3B:
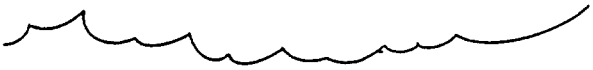
Figure 3B:
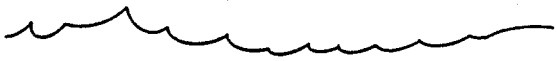
Figure 3B:
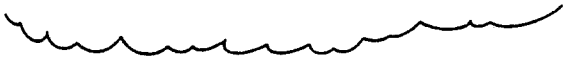
Figure 3B:
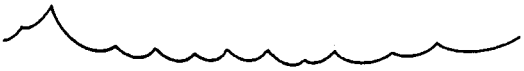
Figure 3B:
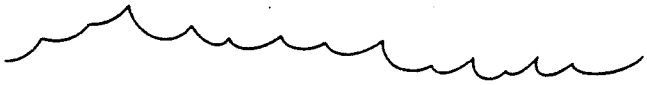
Figure 3B:
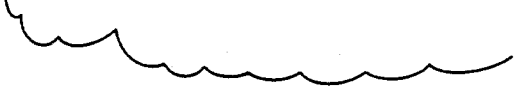
Figure 3B:
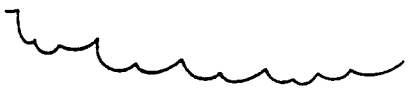
Figure 3B:
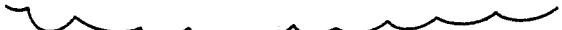
Figure 4:
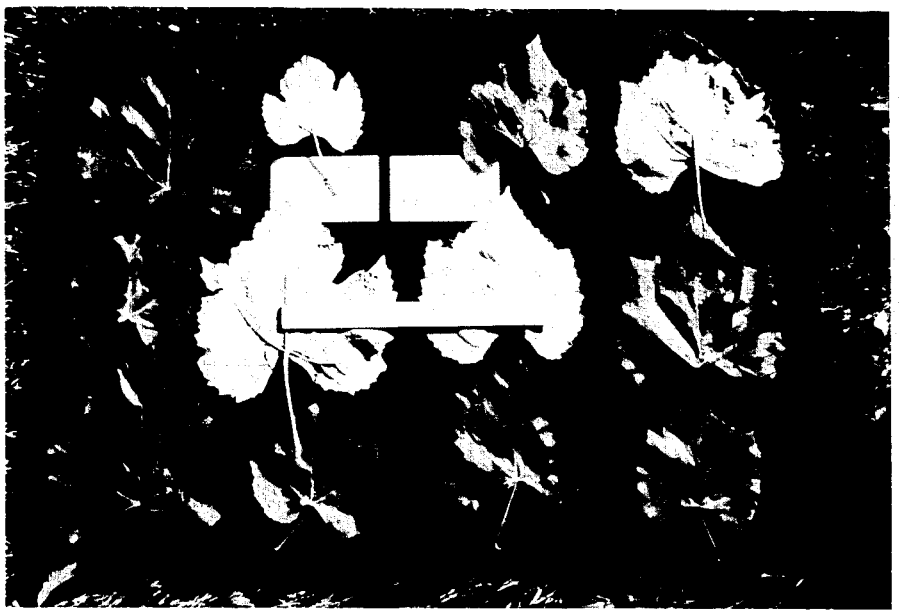
FIG. 4 is a photograph of the leaves of Kat.E.Lin and Concord to illustrate the range in leaf shape.
Figure 6:
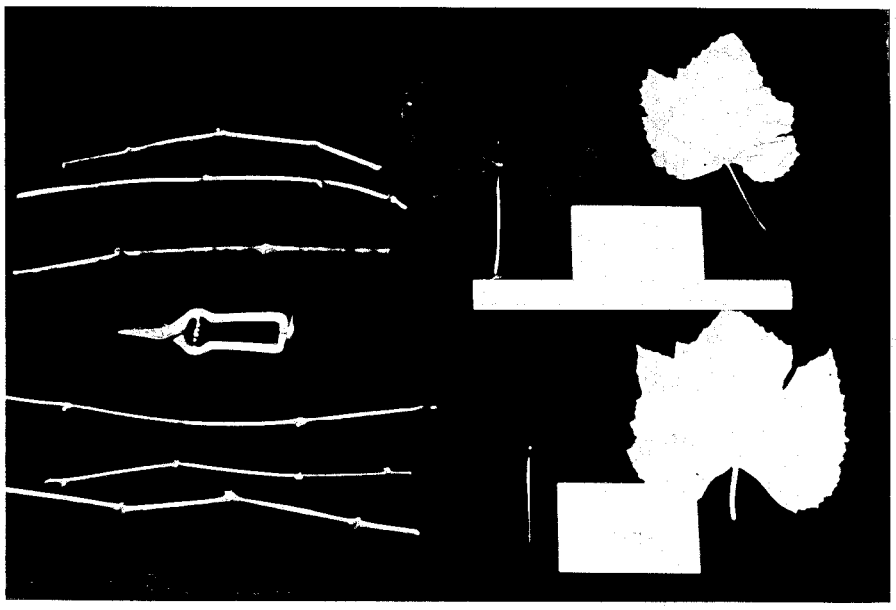
FIG. 6 is a photograph of leaves and canes of Kat.E.-Lin and Concord to illustrate the differences in colour and dimension.
Figure 5:
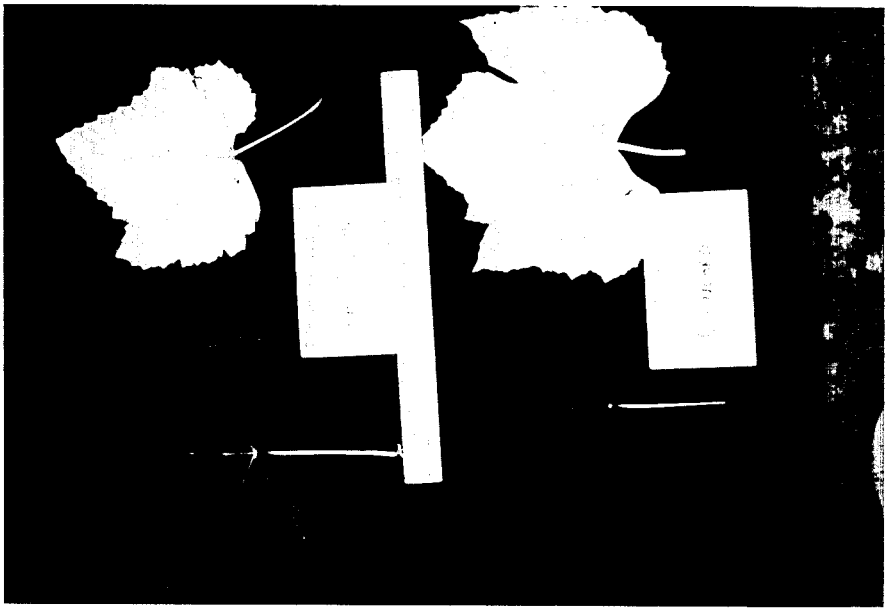
FIG. 5 is a photograph of the leaves of Kat.E.Lin and Concord to illustrate the colour and texture of both surfaces.

| KAT.E.LIN | CONCORD |
|---|---|
| **VINE:** | |
| General | |
| large, vigorous | vigorous |
| 1.5 kg/vine 1 yr wood | 1.2 kg/vine |
| trained to 6-cane Kniffin | 6-cane Kniffin |
| production 7–8 kg/vine | 7–8 kg/vin |
| Bark - dark brown (RHSCC 200A) | dark brown (RHSCC 200A) |
| **CANES:** | |
| Colour | |
| light Almond Shell (RHSCC 165A,B) | light Squirrel, Hazelnut Brown (RHSCC 166A,B,C) |
| Size (See Figure 6) | |
| width at node | |
| 12 mm | 10 mm |
| width at internode | |
| 9 mm | 7 mm |
| Size | |
| length of internode | |
| 12 cm | 10 cm |
| average can length | |
| 2.5–3 m | 2–2.5 m |
| Fruitfulness position | |
| clusters on each shoot | after node 1 from |
| after node 1 from base | from the base |
| 3–4 clusters/shoot | 2–3 clusters/shoot |
| | rarely 4 |
| **TENDRILS:** | |
| Length | |
| 11–13 cm | 11–13 cm |
| Thickness | |
| 5–6 mm | 5–6 mm |
| Colour | |
| same brown as the mature cane (RHSCC 165A,B) | same brown as the mature cane (RHSCC 166A,B,C) |
| **FOLIAGE:** | |
| Hairiness (See Figure 5) | |
| Upper surface | |
| smooth, glabrous | smooth, glabrous |
| Lower surface | |
| dense matted felty | dense matted felty |
| white/grey | rufous |
| Mature leaf (See Figure 4) | |
| Shape | |
| cuneo-truncate | cuneiform |
| (length = width) | (length > width) |
| ($\sigma$ = 98.6°) | ($\sigma$ = 84.4°) |
| Size | |
| generally large | medium-large |
| (>400 cm$^2$) | (>300 cm$^2$) |
| Lobes | |
| generally two shallow | generally entire |
| superior lobes | (SS = SI > 0.85) |
| (SS > 0.7 < 0.8, SI > 0.9) | |
| Petiolar sinus (see Fig. 2A,B) | |
| non-parallel, acute | non-parallel, |
| V-shaped ($\Sigma$ = 153°) | flattened ($\Sigma$ = 132°) |
| Surface | |
| smooth, slightly bullate | smooth, slightly bullate |
| Contour | |
| flat | slightly convex |
| Teeth (see Fig. 3A,B) | |
| coarse, pointed to | pointed, shallow, |
| slightly concave with | tip of vein beyond |
| vein extension beyond | the lamina green |
| the lamine red | |
| uneven size but generally | regular, average size |
| wide (length/width:0.3–0.5) | (length/width:0.5–0.7) |
| Colour (See Fig. 4,5) | |
| dark yellow green | dark green |
| RHSCC 137A,B with veins | RHSCC 139 A,B with |
| contrasting at RHSCC | veins contrasting at |
| 151A,B | RHSCC 139D |
| **FLOWERS:** | |
| Bloom | |
| June 18–20 | June 18–20 |
| Position | |

-continued

Figure 8:
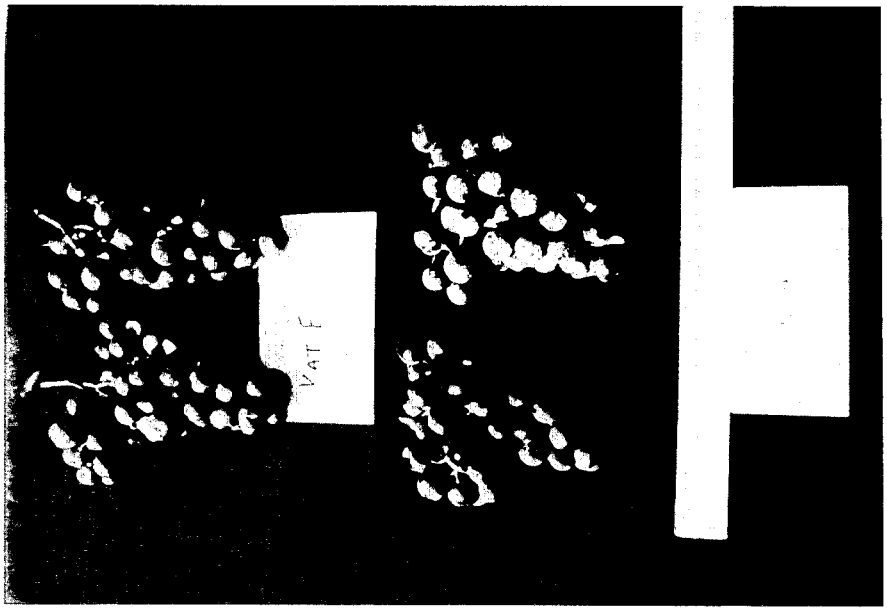
FIG. 8 is a photograph of the clusters of Kat.E.Lin and Concord to illustrate the differences in colour.
Figure 7:
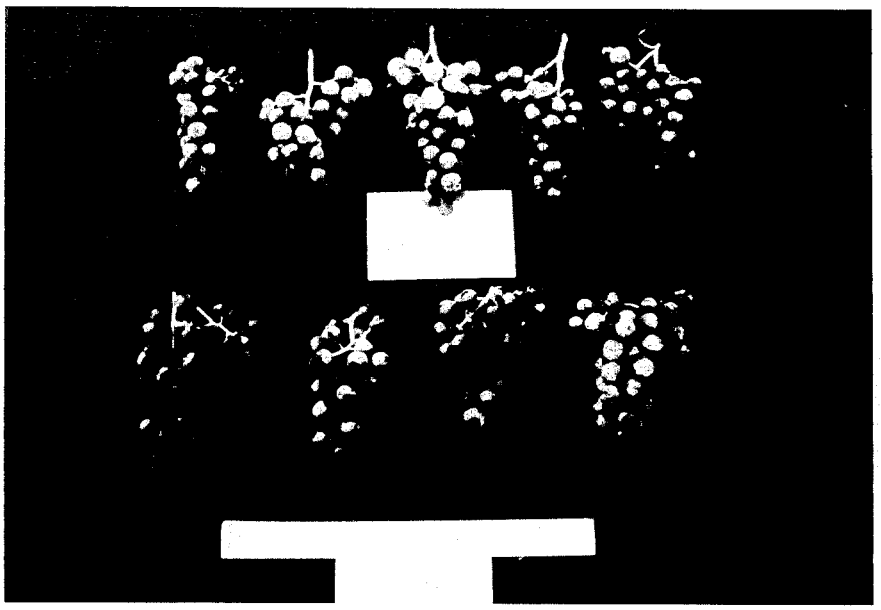
FIG. 7 is a photograph of the clusters of Kat.E.Lin and Concord to illustrate the range in shape and the differences in colour.
Figure 9:
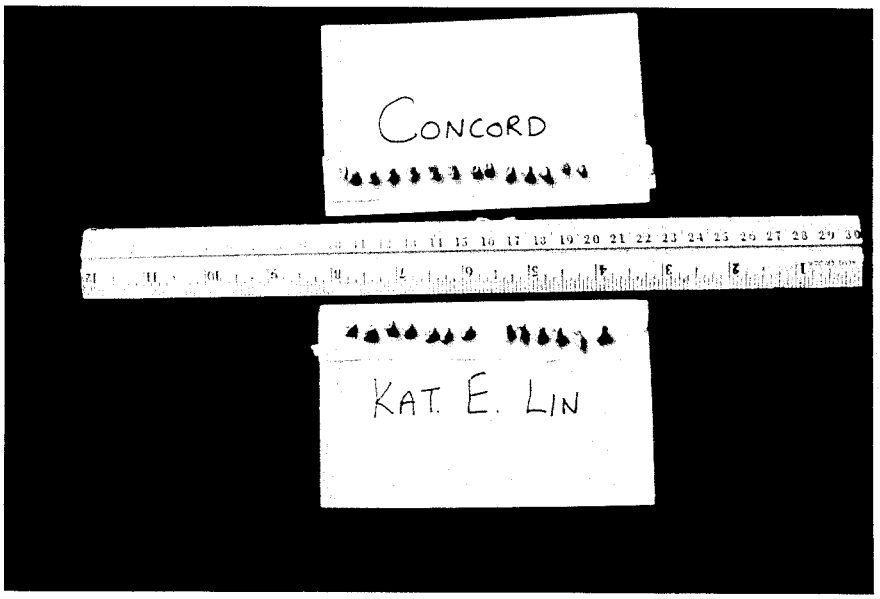
FIG. 9 is a photograph of the seeds of Kat.E.Lin and Concord to illustrate the differences in colour, size and shape.

| KAT.E.LIN | CONCORD |
|---|---|
| nodes 2–8 on 1 yr cane | nodes 2–8 |
| 3–4 bunches/shoot | 2–3 bunches/shoot |
| Quality | |
| hermaphroditic | hermaphroditic |
| self fertile | self fertile |
| **FRUIT:** | |
| Peduncle | |
| medium 3–4 mm diameter | medium to heavy 4–5 mm in diameter |
| bright green (RHSCC 144A,B) | green (RHSCC 136B,C) |
| Cluster | |
| Size (See Fig. 8) | |
| small to medium | small to medium |
| 14–18 cm | 12–16 cm |
| Shape (See Fig. 7) | |
| winged with shoulder occasionally equal to half length of main cluster | winged with shoulder occasionally equal to ⅓ to ½ length of main cluster |
| 2♂, 3♂ clusters usually conical | 2♂, 3♂ clusters usually conical |
| Weight | |
| 125–250 g | 125–250 g |
| Density | |
| loose | full but not tight |
| Berries | |
| Size | |
| medium | medium |
| 16 mm diameter | 17 mm diameter |
| Weight | |
| medium | medium |
| 2.7 g | 3.4 g |
| Shape (See Figure 7,8) | |
| round to oblate | round to oblate |
| Flesh texture | |
| non-adherent slipskin | non-adherent slipskin |
| firmer than Concord | typical of slipskin |
| gelatinous, green | gelatinous, pale green |
| seeds separate relatively easily from flesh | seeds separate with difficulty |
| Flesh Quality | |
| 21.8°Brix Sept. 27, 1988 | 18.5°Brix/1988 |
| 20.8°Brix Oct. 4, 1989 | 16.2°Brix/1989 |
| 19.0°Brix Sept. 30, 1990 | 15.5°Brix/1990 |
| Skin | |
| firm but edible | tough |
| Brush | |
| white | white |
| medium 3–4 mm | short 2–3 mm |
| Attachment | |
| does not shatter easily at maturity detaches with a wet scar but usually with the skin intact | tends to shatter after full maturity detaches roughly, often leaving torn skin and always a wet scar |
| Flavour/Bouquet | |
| mildly foxy, pleasant mildly aromatic | strong but pleasant intensely aromatic, pungent (used as type specimen for labrusca flavour/aroma) |
| Colour (See Figure 7,8) | |
| Oxblood/maroon RHSCC 187A,B | blue black RHSCC 103A |
| heavy waxy bloom | heavy waxy bloom |
| Maturity | |
| September 25–Oct. 2 | September 30–Oct. 7 |
| **SEEDS:** | |
| Size | |
| 7 × 4 mm | 6 × 4 mm |
| Frequency | |
| 2–3/berry | 4/berry |
| Shape | |
| elongated, gently tapering | stocky, bulky |
| Surface markings (See Figure 9) | |
| ventral | |

-continued

| KAT.E.LIN | CONCORD |
|---|---|
| beige with yellow brown | beige with grey brown |
| perimeter not distinct | perimeter quite distinct |
| distinct raised keel | keel not so prominent, almost flattened |
| Surface markings | |
| dorsal | |
| yellow brown (RHSCC 199A) | grey brown (RHSCC 197A) |
| gently rounded shoulders | heavy rounded |
| no distinct dorsal groove | shoulders, club shaped with distinct dorsal groove |
| gradual tapering to beak | distinct neck to beak |
| dark red/brown at basal | beak uniformly |
| tip of beak (RHSCC 200B) | coloured |

The new mutant is vigorous and productive and ripens well before frost. Fruiting wood withstands temperatures below −18° C. It produces fairly large open bunches with large shoulders. The fruit is red to dark maroon/oxblood red. It has high dissolved solids (Brix readings), exceeding those of many varieties noted in the Grape and Wine Research Summary for the year 1984, published by the Horticultural Research Institute of Ontario, Vineland Station, Ontario. The plant is resistant to mildew and does not require thinning to attain commercially acceptable berry size or fruit quality. The fruit has a long shelf life and has proven an excellent product for jam, jelly and sweet dessert wine.

We claim:

1. A new and distinct variety of grapevine, substantially as herein shown and described, characterized by excellent vigor and producitvity, early ripening, hardiness to below −18° C. temperatures, mildew resistant, long shelf life and high sugar content.

* * * * *

α = ANGLE OF L1 TO L2
β = ANGLE OF L2 TO L3
γ = ANGLE OF L3 TO L4
Σ = SUM OF α + β + γ
σ = SUM OF α + β
r = D × S
SI = si / L3
SS = ss / L2

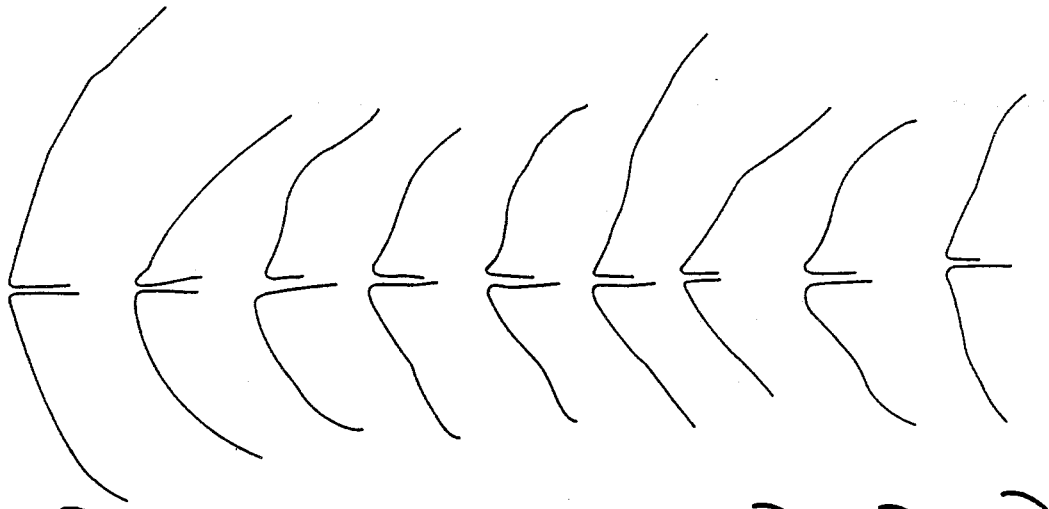
FIG. 2B(a)
FIG. 2B(b)
FIG. 2B(c)
FIG. 2B(d)
FIG. 2B(e)
FIG. 2B(f)
FIG. 2B(g)
FIG. 2B(h)
FIG. 2B(i)
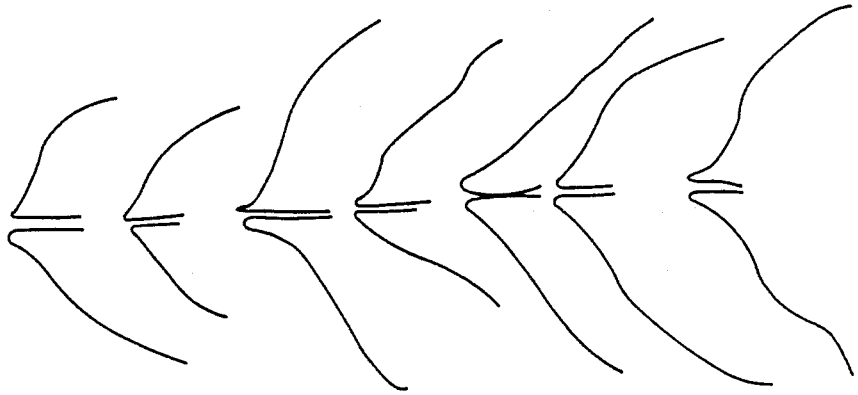
FIG. 2A (a)
FIG. 2A(b)
FIG. 2A(c)
FIG. 2A(d)
FIG. 2A(e)
FIG. 2A(f)
FIG. 2A(g)

UNITED STATES PATENT AND TRADEMARK OFFICE

CERTIFICATE OF CORRECTION

PATENT NO. : Plant 7,644

DATED : September 10, 1991

INVENTOR(S) : LOUNSBURY, SR. et al.

It is certified that error appears in the above-identified patent and that said Letters Patent is hereby corrected as shown below:

| | |
|---|---|
| Column 2, line 15 | Delete "growin", insert therefor -- growing -- |
| Column 2, line 35 | Delete "foolow", insert therefor -- follow -- |

On title page:

[54] Delete "GRAPVINE", insert therefor -- GRAPEVINE --

Signed and Sealed this

Twenty-second Day of June, 1993

*Attest:*

Michael K. Kirk

MICHAEL K. KIRK

*Attesting Officer*

*Acting Commissioner of Patents and Trademarks*